US010372802B2

(12) United States Patent
Buurman

(10) Patent No.: US 10,372,802 B2
(45) Date of Patent: Aug. 6, 2019

(54) GENERATING A REPORT BASED ON IMAGE DATA

(75) Inventor: Johannes Buurman, 's-Hertogenbosch (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1487 days.

(21) Appl. No.: 14/006,686

(22) PCT Filed: Mar. 15, 2012

(86) PCT No.: PCT/IB2012/051232
§ 371 (c)(1),
(2), (4) Date: Sep. 23, 2013

(87) PCT Pub. No.: WO2012/131518
PCT Pub. Date: Oct. 4, 2012

(65) Prior Publication Data
US 2014/0013199 A1 Jan. 9, 2014

(30) Foreign Application Priority Data
Mar. 25, 2011 (EP) ...................................... 11159820

(51) Int. Cl.
G06F 17/24 (2006.01)
G06F 19/00 (2018.01)
(Continued)

(52) U.S. Cl.
CPC .......... G06F 17/243 (2013.01); G06F 19/321 (2013.01); G16H 15/00 (2018.01); G16H 10/60 (2018.01)

(58) Field of Classification Search
CPC .................................................. G06F 17/243
(Continued)

(56) References Cited

U.S. PATENT DOCUMENTS 7,624,027 B1 11/2009 Stern et al.
8,788,292 B2 7/2014 Bourdeaux et al.
(Continued)

FOREIGN PATENT DOCUMENTS

EP 2169577 A1 3/2010
JP 2009069977 A 4/2009
(Continued)

OTHER PUBLICATIONS

Lovis, C. et al. "Clinical Documents: Atrribute-Values Entity Representation, Context, Page Layout and Communication." AMIA 2003 Symposium Proceedings—p. 396-400.
(Continued)

Primary Examiner — James J Debrow

(57) ABSTRACT

A system for generating a report based on image data is disclosed. A template selector (1) selecting a template from a plurality of templates, the template defining a structure for the report and data fields to be filled in for the report, wherein the template further defines associations between data fields and view descriptors, wherein a view descriptor defines an image type and a presentation mode of the image type. A data field presenter (2) presenting a representation of the data fields of the template to a user. An image dataset selector (4) automatically selecting at least one image dataset having the image type defined by the view descriptor associated with the selected at least one data field. A view generator (5) automatically generating a view of the at least one selected image dataset based on the presentation mode defined by the view descriptor associated with the selected at least one data field. A report generator (7) for generating the report based on the template and the data provided by the user.

13 Claims, 4 Drawing Sheets

(51) Int. Cl.
   *G16H 15/00*   (2018.01)
   *G16H 10/60*   (2018.01)

(58) Field of Classification Search
   USPC .......................................................... 715/226
   See application file for complete search history.

(56) References Cited

U.S. PATENT DOCUMENTS

| | | | |
|---|---|---|---|
| 9,292,655 B2* | 3/2016 | Arazi | G06F 19/3487 |
| 2003/0194057 A1* | 10/2003 | Dewaele | G06T 7/0012 |
| | | | 378/210 |
| 2004/0186747 A1 | 9/2004 | Nakano et al. | |
| 2006/0239522 A1* | 10/2006 | Ferrant | G06T 7/0083 |
| | | | 382/128 |
| 2007/0038929 A1* | 2/2007 | Miyazawa | G06F 17/00 |
| 2007/0168223 A1 | 7/2007 | Fors et al. | |
| 2009/0106047 A1 | 4/2009 | Bay et al. | |
| 2010/0114598 A1 | 5/2010 | Oez | |
| 2010/0138239 A1* | 6/2010 | Reicher | G06F 17/243 |
| | | | 705/3 |
| 2011/0244415 A1* | 10/2011 | Batesole | A61C 7/00 |
| | | | 433/24 |
| 2012/0035963 A1* | 2/2012 | Qian | G06F 19/3487 |
| | | | 705/3 |

FOREIGN PATENT DOCUMENTS

| | | |
|---|---|---|
| JP | 2009078050 A | 4/2009 |
| JP | 2009271621 A | 11/2009 |
| WO | 2010019351 A1 | 2/2010 |

OTHER PUBLICATIONS

George, J. "An Ontology Model for Clinical Documentation Templates." Thesis—2005 Massachusetts Institute of Technology. Department of Health Sciences and Technology.

Demner-Fushman, D. et al. "What can natural language processing do for clinical decision support?" Journal Biomedical Informatics. Oct. 2009; 42(5): 760-772.

\* cited by examiner

Munchausen, S
44765451

Procedure  MR Prostate
Date 2009-02-02
Modality MR
Site Pelvis
Modifier Enhanced
Technique
Field_strength: 3.0T  Contrast_media  Name: Gadolinium  Amount: 10 ml  Image_quality Statisfactory
Description
Using a phased array coil with an endorectal coil small field-of-view imaging of the prostate was performed using the following sequences; axial T1-weighted, axial T2-weighted, sagittal T2-weighted, oblique coronal T2-weighted. Axial T1-weighted images through the prostate were obtained before and after the intravenous administration of 10 ml of Gd. DTPa.

Clinical information
Prostate cancer.

Comparison
Comparison_exam  Date : 2009-01-01     Exam_type : MR     ← 401
Comparison_exam  Date : 2002-07-17     Exam_type : CT

Findings
Prostate
Size              Measurement : 51 mm
Volume            19 cc
Central_gland     Early_enhancement_with_washout
Peripheral_zone   T2_hypointensity :low signal on T2-weighted images

Impression
Suggestion of prostate cancer.     402
Recommendation    US guided biopsy

Key Images

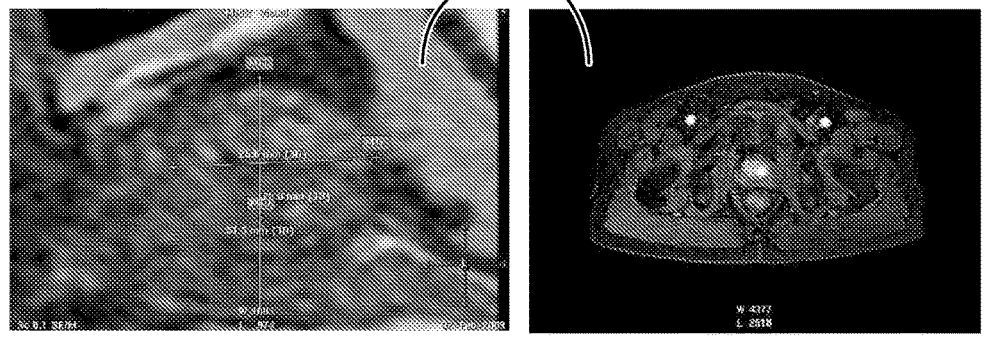

FIG. 4

GENERATING A REPORT BASED ON IMAGE DATA

This application is a national stage application under 35 U.S.C. § 371 of International Application No. PCT/IB2012/051232 filed on Mar. 15, 2012 and published in the English language on Oct. 4, 2012 as International Publication No. WO/2012/131518, which claims priority to European Application No. 11159820.7 filed on Mar. 25, 2011, the entire disclosures of which are incorporated herein by reference.

FIELD OF THE INVENTION

The invention relates to generating a report based on image data.

BACKGROUND OF THE INVENTION

In current radiology, images are created by an operator of medical imaging equipment in response to a request. In response to this request, images are made and subsequently, a report is created. The request typically describes a modality and an area in the body, and can be extended with a description of complaints or a possible diagnosis to be confirmed or excluded. In most cases the images are created by technologists, and the report is later made in a reading room by the radiologist. In some cases (for example, in case of ultrasound studies) the radiologist may perform the imaging himself.

Subsequently, the report is created. The common way to do this is by dictation, where either speech recognition or transcription is used to create a written report. The content of this report may be formalized to some extent. However, the resulting text is not structured.

Recently, a trend has appeared towards structured reporting. Herein, the report is structured so that other applications can make use of the information contained within. A recent initiative by RSNA is to publish a set of templates for the structure of the reports for a number of different applications.

An advanced area for reporting is breast cancer diagnosis, where the ACR's Breast Imaging Reporting and Data System (BI-RADS) describes the wording and structure of the report for the three modalities Mammography (X-Ray), Ultrasound, and MRI. Parts of BI-RADS have been incorporated into the DICOM Structured Reporting for Mammography CAD SOP Class definition. Analysis packages like DynaCAD (Invivo), CADStream (Merge), and B-CAD (Medipattern) use a dedicated user interface to fill in a BI-RADS form and link the reported findings to key images. Philips IntelliSpace Breast is capable of doing the same, for all modalities. It encodes the content in a DICOM Structured Report.

In Ultrasound, DICOM structured Reports are used to store reports generated on the cart, for instance in cardiology. However, all these user interfaces are specific to the area of application.

SUMMARY OF THE INVENTION

It would be advantageous to have an improved system for generating a report based on image data. To better address this concern, a first aspect of the invention provides a system comprising a template selector for selecting a template from a plurality of templates, the template defining a structure for the report and data fields to be filled in for the report, wherein the template further defines associations between data fields and view descriptors, wherein a view descriptor defines an image type and a presentation mode of the image type;

a data field presenter for presenting a representation of the data fields of the template to a user, a data field selector for selecting at least one of the data fields;

an image dataset selector for automatically selecting at least one image dataset having the image type defined by the view descriptor associated with the selected at least one data field;

a view generator for automatically generating a view of the at least one selected image dataset based on the presentation mode defined by the view descriptor associated with the selected at least one data field;

a user input unit for enabling the user to provide input for a content of the selected at least one data field during display of the generated view;

a report generator for generating the report based on the template and the data provided by the user.

The use of templates to automatically select at least one image dataset and generate a view based on a presentation mode corresponding to a selected at least one data field makes it particularly efficient to review the appropriate images and to create the desired report.

The template may further define associations between data fields and measurement descriptors, wherein a measurement descriptor defines a measurement to be performed on the image type associated with the data field;

the system further comprising a measurement tool for performing a measurement based on the selected at least one image dataset, and the measurement descriptor, to obtain a measurement data;

wherein the report generator is arranged for using the measurement data to fill in the at least one data field.

The collection of the relevant information to be included in a report may be further enhanced by automatically launching an appropriate measurement tool that can provide the information needed for the report. The measurement tool may function completely automatic or in an interactive mode. In the interactive mode, the measurement tool may be operatively connected to the user input unit, and the measurement tool may be arranged for performing the measurement also based on a user input.

The system may comprise a report storage unit for storing the report in a data record associated with the subject of the at least one image dataset. This way, an efficient link between a picture archiving and communication system (PACS) and a hospital information system (HIS) or radiology information system (RIS) may be established, for example. The images may be retrieved from the PACS, while the created reports may be stored in the HIS or RIS.

To that end, the system may comprise a first communication module for communicating with a picture archiving and communications system (PACS) comprising an image database and a second communication module for communicating with an information system comprising a radiology or hospital information system (RIS/RIS).

The report generator may comprise a natural language generator for generating natural language comprising a representation of the data of the at least one data field. This way, the resulting report is easier to read.

The report generator may be arranged for including a presentation of the at least one selected image dataset based on the view generated by the view generator and/or a presentation mode defined by the view descriptor associated with the selected at least one data field. This allows the report to be automatically illustrated.

The user input unit may comprise a speech recognition module for enabling the user to supply information for at least one of the data fields using speech recognition. This allows the user to provide input for the report more efficiently.

In another aspect, the invention provides a workstation comprising the system set forth.

In another aspect, the invention provides a method of generating a report, comprising selecting a template from a plurality of templates, the template defining a structure for the report and data fields to be filled in for the report, wherein the template further defines associations between data fields and view descriptors, wherein a view descriptor defines an image type and a presentation mode of the image type;

presenting a representation of the data fields of the template to a user, selecting at least one of the data fields;

automatically selecting at least one image dataset having the image type defined by the view descriptor associated with the selected at least one data field;

automatically generating a view of the at least one selected image dataset based on the presentation mode defined by the view descriptor associated with the selected at least one data field;

enabling the user to provide input for a content of the selected at least one data field during display of the generated view; and generating the report based on the template and the data provided by the user.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the image acquisition apparatus, the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings.

FIG. 4 shows a report.

DETAILED DESCRIPTION OF EMBODIMENTS

Figure 1:
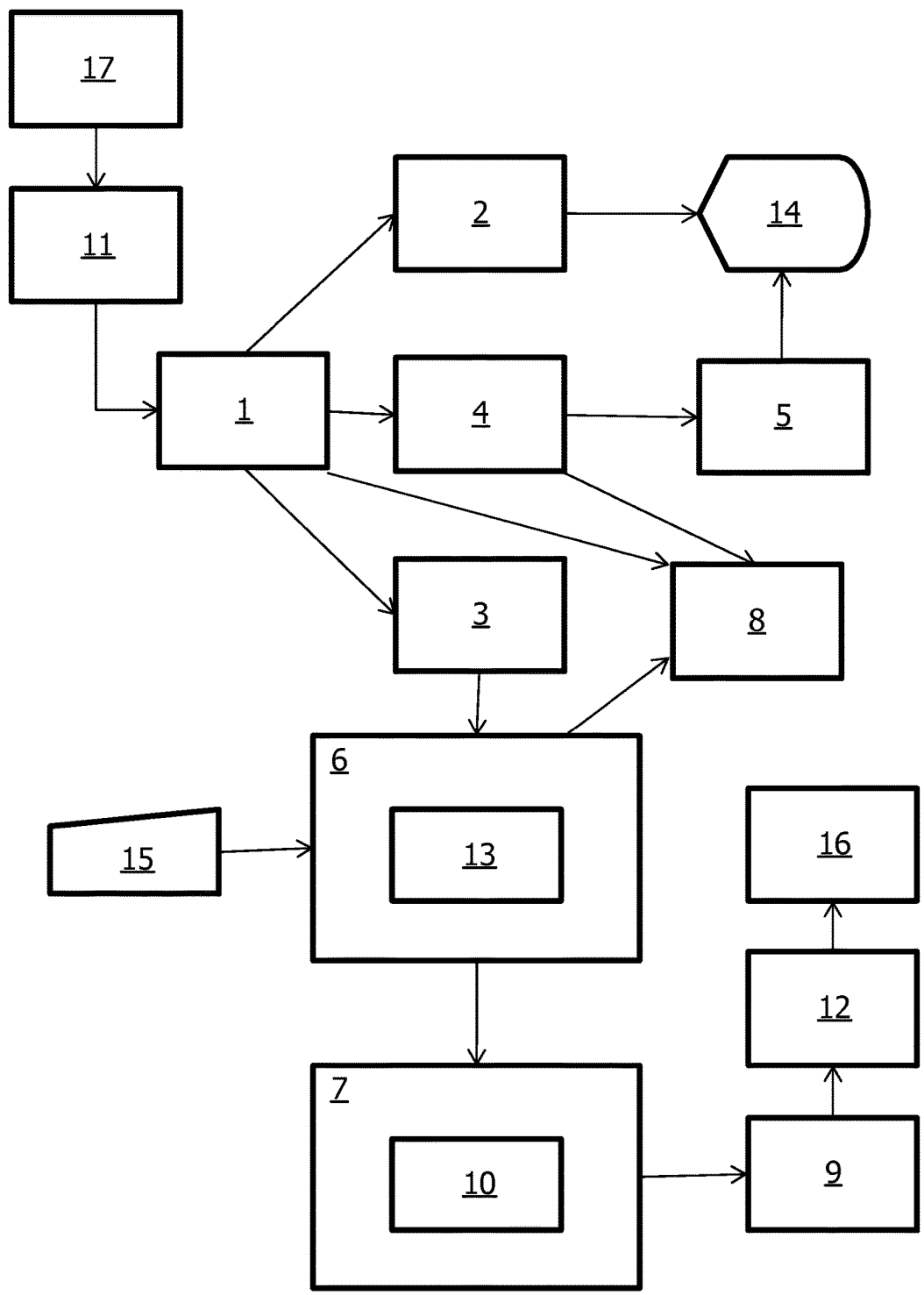
FIG. 1 shows a diagram of a system for generating a report based on image data.

FIG. 1 shows a block diagram illustrating some aspects of a system for generating a report based on image data. To be able to describe the system more clearly, only the most relevant parts of the system have been represented in the figure, and only some of the interrelations between those parts have been drawn. It is noted that variations of the system described are possible. Only an example implementation is shown in the drawing. Some of the elements shown are optional. The system may be implemented on a computer system, for example using software. The computer system may comprise a distributed system, or a workstation.

The system may comprise a template selector 1 arranged for selecting a template from a plurality of templates. The template may define a structure for the report and data fields to be filled in for the report. The template may further define associations between data fields and view descriptors, wherein a view descriptor defines an image type and a presentation mode of the image type. The template selector 1 may be coupled to a picture archiving and communications system (PACS) 17, for example. The user may be enabled to select an image study from the PACS 11 and provide it as input to the template selector 1. In another example, the user may be enabled to select a template from a RIS worklist, and retrieve the image data from a PACS based on said worklist. The template selector may be arranged for analyzing the image data and based on the type of study determining the kind of report, and thus the template, needed. The template selector 1 may also be coupled to another information system 16, for example a radiology information system (RIS) or hospital information system (HIS). The RIS/HIS 16 may contain a document received from the referring physician, asking for a particular study type. The template selector 1 may be arranged for selecting the template based on such information. The template selector 1 may also be arranged for enabling the user to select a template. Also, a user interface may be provided to allow selection of a particular patient or a particular case from a task list, for example.

The system may further comprise a data field presenter 2. The data field presenter 2 may be arranged for presenting a representation of the data fields of the template to a user. For example, the data fields may be presented as an electronic form in which the user can select user interface elements, such as widgets, drop-down boxes, and text entry fields, corresponding to the data fields specified by the template.

The system may further comprise a data field selector 3 arranged for selecting at least one of the data fields. This selection may take place based on, for example, a mouse click on the field to be selected. The selector 3 may also be arranged for automatically selecting the fields, for example in a sequential order. The order may be specified in the template and may be overruled by the user.

The system may further comprise an image dataset selector 4 that may be arranged for automatically selecting at least one image dataset having the image type defined by the view descriptor associated with the selected at least one data field. For example, the image dataset selector 4 may be arranged for searching an image dataset satisfying a set of search criteria specified by or based on the search type. Herein, the image dataset selector 4 may be arranged for searching images for a particular patient to whom the report applies. Also, the image dataset selector 4 may be arranged for selecting a historic image or a reference image, for example. Such a historic or reference image may be shown together with the current patient's data in order to facilitate a comparison.

The system may comprise a view generator 5 for automatically generating a view of the at least one selected image dataset. This view is generated based on the presentation mode defined by the view descriptor associated with the selected at least one data field. For example, the selected image dataset may be processed to render a particular view, such as a slice view or a maximum intensity projection (MIP) view, as specified by the view descriptor contained in the template.

The system may comprise a display 14 for displaying the generated view. Moreover, the display 14 may be arranged for displaying the representation of the data fields provided by the data field presenter 2.

The system may comprise a user input unit 6 for enabling the user to provide input for a content of the selected at least one data field during the display of the generated view. The user input unit 6 may be arranged for receiving input from a user input device 15, such as a keyboard, a mouse, or a microphone.

The system may comprise a report generator 7 for generating the report. The report generator 7 is arranged for processing the template and the data provided by the user. This information may be combined with a style sheet, for example, to render the report. The report may be made in a structured form, for example a tabular form or in form of an XML document. The report may also be rendered in a textual form, for example using natural language. The report may be printed on a printer (not shown) or stored to an information system 16. Either or both of the structured form and the textual form may be stored via report storage unit 9.

The template may further define associations between data fields and measurement descriptors. Such a measurement descriptor defines a measurement to be performed on the image type associated with the data field. When the image dataset selector 4 has selected an image dataset having that image type, it becomes possible to perform such measurements automatically or to initialize a software tool to facilitate the measurement using that selected image dataset. To that end, the system may further comprise a measurement tool 8 for performing a measurement based on the selected at least one image dataset, and the measurement descriptor, to obtain a measurement data. The report generator 7 may be arranged for using the measurement data to fill in the at least one data field.

The measurement tool 8 may be operatively connected to the user input unit 6. This way, the measurement tool 8 may allow the user to provide an input to set e.g. points in the image, or otherwise influence the measurement. For example, the template may define a length measurement to be done for a particular bone in a particular kind of x-ray image. The image selector then selects that kind of x-ray image of the patient from the image database, the view generator generates a view showing the bone to be measured, and the measurement tool is launched. For example, the measurement tool shows a message on the screen 14 instructing the user to click on the two far ends of the bone. The measurement tool then draws a line in between the two selected points, shows the line on the display 14, computes the length between the two selected points, and fills in the length between the two points in the prescribed data field represented by the electronic form.

The system may comprise a report storage unit 9 for storing the report in a data record associated with the subject of the at least one image dataset. To this end, the report storage unit may use a data communication module 12 to connect with an information system 16, such as a RIS or HIS. The information system may also be a PACS, because it may be arranged that the report is stored in the PACS.

The report generator 7 may comprise a natural language generator 10 for generating natural language comprising a representation of the data of the at least one data field. Natural language generators are known in the art per se. As an example, the template may comprise a stylesheet defining bits of natural language text with blanks to be filled in by the entries in the data fields.

The report generator 7 may be arranged for including a presentation of the at least one selected image dataset based on the view generated by the view generator 5 and/or a presentation mode defined by the view descriptor associated with the selected at least one data field. For example, an output image of the measurement tool 8 may be included in the report.

The system may comprise a first communication module 11 for communicating with a picture archiving and communications system (PACS) 17 comprising an image database and a second communication module 12 for communicating with an information system 16 comprising a radiology information system (RIS) or a hospital information system (HIS). The templates may be retrieved by the template selector, for example, from the information system 16. The images may be retrieved from the PACS 17. The report may be stored to the information system 16 and/or the PACS 17.

The user input unit 6 may comprise a speech recognition module 13 for enabling the user to supply information for at least one of the data fields using speech recognition. Speech recognition techniques are known in the art per se.

Some, or all, of the functionality may be provided through a workstation. The workstation may be programmed with software representing the parts of the system described herein. The functionality may also be provided via a remote data connection, such as an interactive web application or using a client-server architecture.

Figure 2:
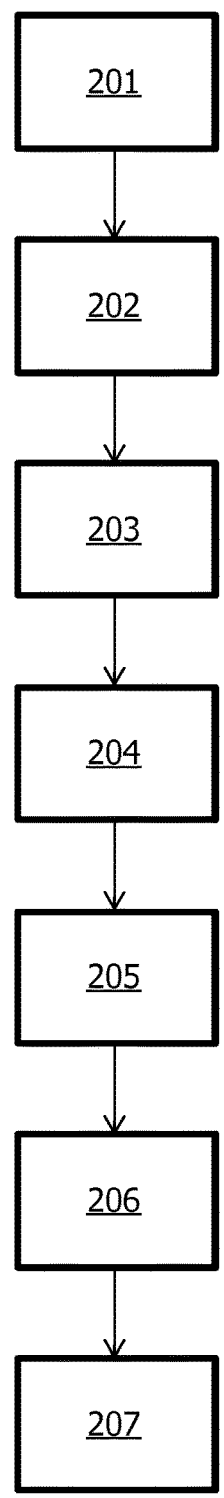
FIG. 2 shows a flowchart of a method of generating a report based on image data.

FIG. 2 shows a flowchart of a method of generating a report. The method comprises the steps of selecting 201 a template from a plurality of templates, the template defining a structure for the report and data fields to be filled in for the report, wherein the template further defines associations between data fields and view descriptors, wherein a view descriptor defines an image type and a presentation mode of the image type; presenting 202 a representation of the data fields of the template to a user; selecting 203 at least one of the data fields; automatically 204 selecting at least one image dataset having the image type defined by the view descriptor associated with the selected at least one data field; automatically generating 205 a view of the at least one selected image dataset based on the presentation mode defined by the view descriptor associated with the selected at least one data field; enabling 206 the user to provide input for a content of the selected at least one data field during display of the generated view; and generating 207 the report based on the template and the data provided by the user. This method may be implemented as a computer program product. The method may be extended or modified based on the functionality disclosed in this description.

RSNA has published a number of templates for structured reporting. They consist of two representations of in total about 100 reports. One version is machine readable, in xml. The other version is a text example of such a report. The machine readable versions may be used as part of the templates described herein. Note that the RSNA templates are only an example. The system disclosed herein can be operated with different templates. For example, the users may be enabled to add their own templates. Moreover, templates may be used that include more and different information in the report than only what is prescribed by the RSNA. For example, templates may be used that include data fields allowing the user to indicate what kind of measurement leads to a certain value.

The reporting system disclosed herein may comprise a template selector that derives, from the data (e.g. image attributes) and/or the request, which report template is appropriate. Then, a reporting workspace may be created that takes the machine-readable version of the template, and based on that:

Derives a data structure that represents the structured report.

Generates a dedicated user interface to fill in the data structure.

For example, the user interface screen may be subdivided into in "tasks" and "forms". Tasks comprise the main screens of the task flow guidance, typically "Procedure", "Clinical Information", "Comparison", "Findings" and "Impression". Forms comprise a subsections in which parts of the report are filled in. The "Findings" tab typically has many subdivisions, which can be created using expanders or a harmonica control, for example.

Generates a style sheet to render the report in a human-readable form. Similarly, a structured version (or plain text version) of the same report can be sent to the reporting system (e.g. RIS) and a picture version to a PACS.

The system set forth may help to ensure consistent, complete and accurate reports: templates may be used to enforce completeness, and measurements are automatically entered into the report. Better information is provided to referring physician: complete, structured report with key images. Management reporting is enabled: It is possible to perform statistics, because the reports have a structured form, values of different reports may be compared and analyzed. Quality assurance can be improved. Also for this purpose, the system can do detailed statistics: e.g about findings, outcomes . . . . Also clinical research is made easier because of the ease in which statistics can be computed for the generated reports. For example, when using structured report format, it can be determined automatically how many patients with a particular diagnosis X had a finding Y.

Figure 3:
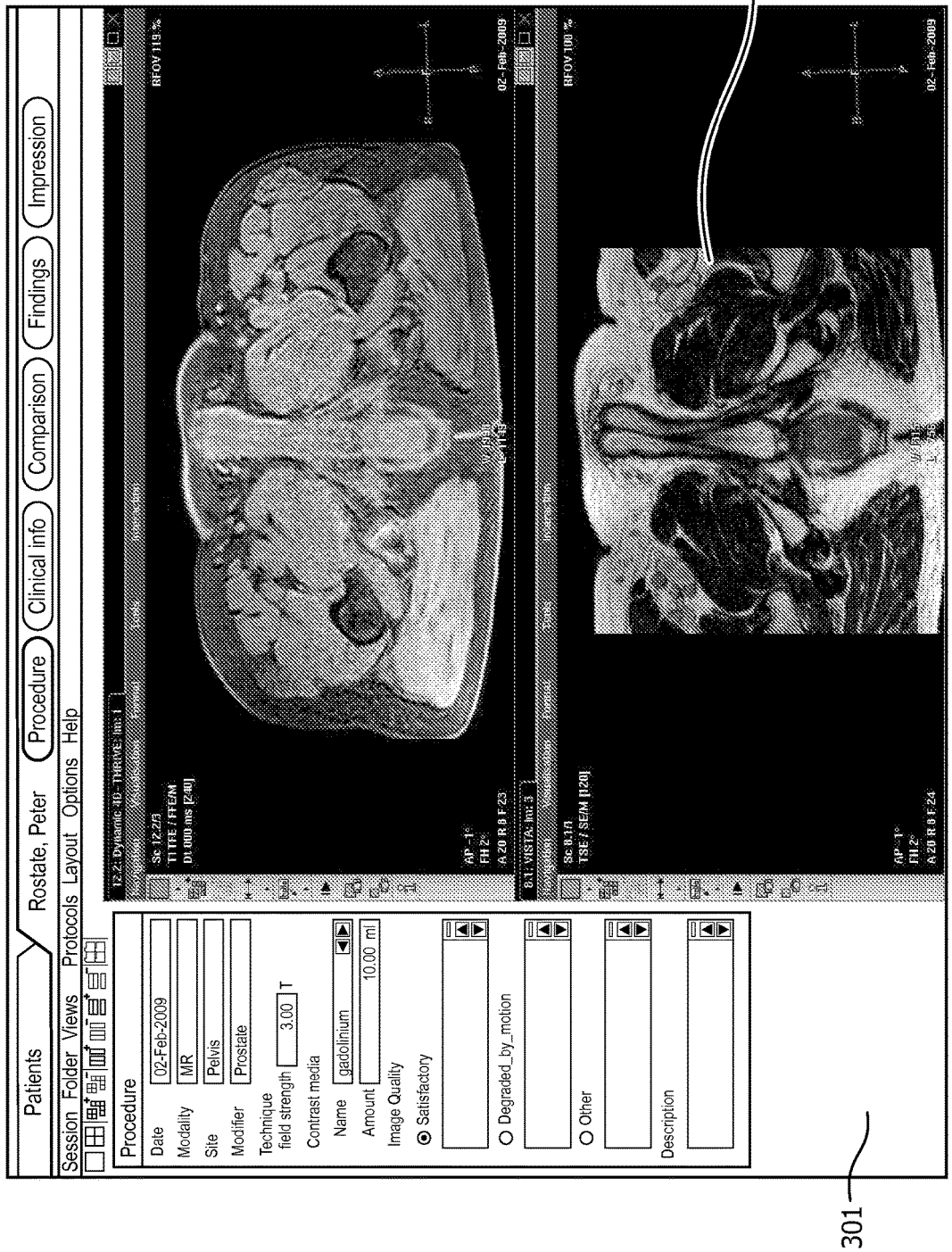
FIG. 3 shows a screen shot.

FIG. 3 shows a screenshot of such an application for a protocol relating to MR Prostate. The panel 301 on the left hand side shows some of the data fields for which data is to be supplied. The panel 302 on the right hand side shows two views of image data, wherein the image data sets have been automatically selected by the image dataset selector 4. The two slices have been generated automatically by the view generator 5, and are displayed automatically. Some of the data fields shown on the left hand panel 301 may be filled in automatically, based on the information already available from metadata of the images (for example: MR field strength), or from information available in the electronic health record (for example: date of birth). The system can automatically include the result of a measurement in the "Findings" section. Because the value is automatically entered into the report, mistakes are eliminated. Also, a key image may be added to the report, based on the template and/or the views. This key image may include annotations showing the measurement or highlighting the important areas.

FIG. 4 illustrates a report rendered by the system disclosed herein. The report is comprises a text portion 401 that is easily readable for a human, such as the referring physician. Some key images 402 are included based on the views generated by the view generator. Also the key images include annotations of measurements performed.

The systems and methods disclosed herein may help to ensure consistent complete and accurate reports, provide better information to referring physician, enable management reporting, enable quality assurance, and enable clinical research. In prior art systems, it may take a long time to build a dedicated solution. Also it is difficult to adopt the user interfaces to a user's own requirements, e.g. adding another measurement is hard or impossible.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for generating a report based on image data, comprising
   a template selector for selecting a template from a plurality of templates, the template defining a structure for the report and data fields to be filled in for the report, wherein the template further defines view descriptors and associations between the data fields and the view descriptors, wherein a view descriptor defines an image type and a presentation mode of the image type;
   a data field presenter for presenting a representation of the data fields of the template to a user,
   a data field selector for selecting at least one of the data fields;
   an image dataset selector for automatically selecting at least one image dataset of the image type defined by the view descriptor associated with the selected, at least one, data field;
   a view generator for automatically generating a view in the presented representation of the data fields of the template of the at least one selected image dataset based on the presentation mode defined by the view descriptor associated with the selected, at least one, data field;
   a user input unit for enabling the user to provide input for the content of the selected, at least one, data field during display of the generated view;
   a report generator for generating the report according to the template from the data automatically included in the presented representation of the data fields including the generated views and the data provided by the user.

2. The system according to claim 1,
   wherein the template further defines associations between data fields and measurement descriptors, wherein a measurement descriptor defines a measurement to be performed on the image type associated with the data field;
   the system further comprising a measurement tool for performing a measurement based on the selected, at least one, image dataset, and the measurement descriptor, to obtain measurement data;
   wherein the report generator is arranged for using the measurement data to fill in the at least one data field.

3. The system according to claim 2, wherein the measurement tool is operatively connected to the user input unit, and wherein the measurement tool) performs the measurement also based on a user input.

4. The system according to claim 1, further comprising a report storage unit for storing the report in a data record associated with the subject of the at least one image dataset.

5. The system according to claim 1, wherein the report generator comprises a natural language generator for generating natural language comprising a representation of the data of the at least one data field.

6. The system according to claim 1, wherein the report generator is arranged for including a presentation of the at least one selected image dataset based on the view generated by the view generator and/or a presentation mode defined by the view descriptor associated with the selected, at least one, data field.

7. The system according to claim 1, comprising a first communication module for communicating with a picture archiving and communications system (PACS) comprising an image database and a second communication module for communicating with an information system comprising a radiology information system (RIS).

8. The system according to claim 1, wherein the user input unit comprises a speech recognition module for enabling the user to supply information for at least one of the data fields using speech recognition.

9. A workstation comprising the system according to claim 1.

10. A method of generating a report, comprising
    selecting a template from a plurality of templates, the template defining a structure for the report and data fields to be filled in for the report, wherein the template further defines view descriptors and associations between the data fields and the view descriptors, wherein a view descriptor defines an image type and a presentation mode of the image type;
    presenting a representation of the data fields of the template to a user,
    selecting at least one of the data fields;
    automatically selecting at least one image dataset of the image type defined by the view descriptor associated with the selected, at least one, data field;
    automatically generating a view in the presented representation of the data fields of the template of the at least one selected image dataset based on the presentation mode defined by the view descriptor associated with the selected, at least one, data field;
    enabling the user to provide input for the content of the selected, at least one, data field during display of the generated view; and
    generating the report from the data automatically included in the presented representation of the data fields including the generated views according to the template and the data provided by the user.

11. A non-transitory storage media comprising a computer program product comprising instructions for causing a processor system to perform the method according to claim 10.

12. The system according to claim 1, wherein the view generated by the view generator based on the presentation mode includes at least one of a group consisting of a slice view and a maximum intensity projection (MIP) view.

13. The method according to claim 10, wherein automatically generating the view based on the presentation mode includes generating at least one of a group consisting of a slice view and a maximum intensity projection (MIP) view.

* * * * *